(12) United States Patent
Rossing

(10) Patent No.: US 7,212,856 B2
(45) Date of Patent: May 1, 2007

(54) REFORMATION TECHNIQUES FOR CAPACITORS OF IMPLANTABLE MEDICAL DEVICES

(75) Inventor: Martin A. Rossing, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 469 days.

(21) Appl. No.: 10/630,002

(22) Filed: Jul. 29, 2003

(65) Prior Publication Data

US 2005/0027319 A1 Feb. 3, 2005

(51) Int. Cl.
*A61N 1/378* (2006.01)
(52) U.S. Cl. .................................................. 607/8
(58) Field of Classification Search ............... 607/1–76
See application file for complete search history.

(56) References Cited

U.S. PATENT DOCUMENTS

| | | | | |
|---|---|---|---|---|
| 5,201,865 A | * | 4/1993 | Kuehn | 607/8 |
| 5,350,405 A | * | 9/1994 | Silvian | 607/8 |
| 5,741,307 A | | 4/1998 | Kroll | 607/5 |
| 5,800,461 A | * | 9/1998 | Menken et al. | 607/7 |
| 5,861,006 A | * | 1/1999 | Kroll | 607/5 |
| 5,899,923 A | * | 5/1999 | Kroll et al. | 607/5 |
| 5,925,068 A | * | 7/1999 | Kroll | 607/29 |
| 6,096,062 A | * | 8/2000 | Silvian | 607/5 |
| 6,283,985 B1 | * | 9/2001 | Harguth et al. | 607/1 |
| 2001/0047190 A1 | | 11/2001 | Harguth et al. | 607/1 |
| 2004/0064157 A1 | * | 4/2004 | Norton | 607/7 |
| 2004/0073264 A1 | * | 4/2004 | Lyden | 607/7 |
| 2004/0186519 A1 | * | 9/2004 | Norton | 607/5 |
| 2004/0225327 A1 | * | 11/2004 | Norton et al. | 607/5 |

* cited by examiner

*Primary Examiner*—Scott M. Getzow
(74) *Attorney, Agent, or Firm*—Michael C. Soldner; Girma Wolde-Michael

(57) ABSTRACT

The invention is directed to techniques for estimating a deformation factor of one or more capacitors in an implantable medical devices (IMD), and techniques for reforming such capacitors. An estimate of the ideal charge time is extrapolated from a first measured charge interval associated with charging the capacitor(s) to a first energy level. The actual charge time to associated with charging the capacitor(s) to a second energy level, e.g., the fully charged state, is measured. The deformation factor is calculated as a ratio of the actual charge interval to the second energy level to the ideal charge time. In some cases, the calculated deformation factor is used to adjust the timing of a future scheduled reformation of the capacitor(s).

31 Claims, 7 Drawing Sheets

REFORMATION TECHNIQUES FOR CAPACITORS OF IMPLANTABLE MEDICAL DEVICES

TECHNICAL FIELD

The present invention relates to implantable medical devices, and more particularly, to implantable medical devices that have one or more capacitors for delivering shocks for defibrillation, cardioversion or the like.

BACKGROUND

Patients who have experienced ventricular fibrillation or who meet a risk profile for ventricular fibrillation are likely candidates for receiving an implantable medical device. An implantable medical device detects an episode of ventricular fibrillation, for example, and delivers one or more electrical shocks to the patient to stop the fibrillation and allow the heart to reestablish a normal sinus rhythm. In general, implantable medical devices deliver a shock at a first energy level upon detecting fibrillation and, if the fibrillation is not stopped, deliver additional shocks at increasing energy levels until the fibrillation is stopped or the programmed progression of shocks has been exhausted. For each shock, one or more defibrillation capacitors are charged to the desired energy level and then discharged to deliver the shock to the patient.

Implantable defibrillators often form part of implantable pacemakers. Implantable pacemaker-cardioverter-defibrillators (PCDs), for example, provide pacing, cardioversion and defibrillation functionality within a fully integrated implantable medical device (IMD). Implantable defibrillators can also form part of other types of IMDs.

One concern with implantable medical devices involves deformation of the defibrillation capacitors. Again, in order to deliver defibrillation shocks, one or more defibrillation capacitors are charged to a specific energy level and then discharged to deliver the energy to the patient as a defibrillation shock. Capacitor deformation, however, affects the ability to charge the defibrillation capacitors, and also affects the ability of the capacitor to effectively store charge. For example, capacitor deformation generally lengthens the amount of time that it takes to charge the capacitors and may reduce the ability of the capacitors to store the charge.

Capacitor reformation techniques have been developed to address the issue of capacitor deformation of defibrillation capacitors. In order to reform the defibrillation capacitors following extended periods of inactivity, a reformation process typically involves fully charging the defibrillation capacitors to repair the capacitors. Conventionally, reformation processes are programmed to occur within the implantable defibrillator at defined intervals, e.g., every three months or so. The reformation process repairs the defibrillation capacitors by rebuilding oxide layers, or the like. Accordingly, following reformation, the defibrillation capacitors should be capable of receiving charge more quickly, ensuring that defibrillation shocks can be delivered in a timely fashion. Unfortunately, however, each reformation process generally shortens the useful life of the defibrillation capacitors.

SUMMARY

In general, the invention is directed to techniques for estimating a deformation factor of one or more capacitors in an implantable medical device (IMD), and techniques for scheduling future reformations based on the estimated deformation factor. In order to estimate the deformation factor of one or more capacitors, an ideal charge time associated with the capacitor(s) is needed, but typically unavailable. Therefore, in accordance with the invention, an estimate of the ideal charge time is extrapolated from a first measured charge interval associated with charging the capacitor(s) to a first energy level. The deformation effects typically do not manifest at lower energies of charge. Therefore, by extrapolating the first charge time in order to estimate an ideal charge time associated with charging the one or more capacitors to a second energy level, a fairly accurate estimate of the ideal charge time is obtained.

Then, the actual charge time associated with charging the capacitor(s) to a second energy level, e.g., the fully charged state, is measured. The deformation factor is calculated as a ratio of the actual charge interval to the second energy level over the ideal charge time the second energy level. In some cases, the calculated deformation factor is used to adjust the timing of a future scheduled capacitor reformation cycle.

In one embodiment, the invention is directed to a method comprising measuring a first charge interval associated with charging one or more capacitors of an implantable medical device to a first energy level and extrapolating the first charge interval to estimate an ideal charge time associated with charging the one or more capacitors to a second energy level. The method also includes measuring a second charge interval associated with charging the one or more capacitors to the second energy level, and generating a deformation factor as a ratio of the second charge interval to the ideal charge time.

In another embodiment, the invention provides a method comprising calculating a deformation factor associated with one or more capacitors in an implantable medical device, and adjusting a scheduled time associated with a next reformation process on the one or more capacitors based on the deformation factor.

In another embodiment, the invention provides an implantable medical device comprising one or more capacitors, a charge circuit to charge the one or more capacitors, and a charge measurement device to measure charge across the one or more capacitors. The implantable medical device also includes a processor to measure a first charge interval associated with charging the one or more capacitors a first energy level, extrapolate the first charge interval to estimate an ideal charge time associated with charging the one or more capacitors to a second energy level, measure a second charge interval associated with charging the one or more capacitors to the second energy level, and generate a deformation factor as a ratio of the second charge interval to the ideal charge time.

In another embodiment, the invention provides an implantable medical device comprising one or more capacitors, a charge circuit to charge the one or more capacitors, and a charge measurement device to measure charge across the one or more capacitors. The implantable medical device also includes a processor to calculate a deformation factor of the one or more capacitors, and adjust a scheduled time associated with a next reformation process on the one or more capacitors based on the deformation factor.

If implemented in software, the invention may be embodied in a computer-readable medium. Therefore, the invention also contemplates a computer-readable medium comprising executable instructions that when executed in an implantable medical device cause the device to measure a first charge interval associated with charging one or more capacitors of the implantable medical device to a first energy level, extrapolate the first charge interval to estimate an ideal charge time associated with charging the one or more capacitors to a second energy level, measure a second charge interval associated with charging the one or more capacitors to the second energy level, and generate a deformation factor as a ratio of the second charge interval to the ideal charge time.

In another embodiment, the invention provides a computer-readable medium comprising executable instructions that when executed in an implantable medical device cause the device to calculate a deformation factor associated with one or more capacitors in the implantable medical device, and adjust a scheduled time associated with a next reformation process on the one or more capacitors based on the deformation factor.

In another embodiment, the invention provides an implantable medical device comprising one or more capacitors, means for charging the one or more capacitors, and means for measuring charge across the one or more capacitors. The implantable medical device also includes means for measuring a first charge interval associated with charging the one or more capacitors a first energy level means for extrapolating the first charge interval to estimate an ideal charge time associated with charging the one or more capacitors to a second energy level, means for measuring a second charge interval associated with charging the one or more capacitors to the second energy level, and means for generating a deformation factor as a ratio of the second charge interval to the ideal charge time.

In another embodiment, the invention provides an implantable medical device comprising one or more capacitors, means for charging the one or more capacitors, and means for measuring charge across the one or more capacitors. The implantable medical device also includes means for calculating a deformation factor of the one or more capacitors, and means for adjusting a scheduled time associated with a next reformation process on the one or more capacitors based on the deformation factor.

The details of one or more embodiments of the invention are set forth in the accompanying drawings and the description below. Other features, objects, and advantages of the invention will be apparent from the description and drawings, and from the claims.

DETAILED DESCRIPTION

The present invention is directed to techniques for estimating deformation factors of capacitors in implantable medical devices (IMDs), and techniques for reforming such capacitors. Capacitor deformation affects the ability to charge the capacitors. In particular, capacitor deformation generally lengthens the amount of time that it takes to charge the capacitors. For this reason, capacitor reformation techniques are used to reform the capacitors of an IMD following extended periods of inactivity. For example, a reformation process typically involves fully charging the capacitors in the IMD in order to repair the capacitors, e.g., rebuilding oxide layers, or the like.

In accordance with the invention, the deformation factor of one or more capacitors in an IMD is calculated during the reformation process. Alternatively, the deformation factor could be calculated during delivery of therapeutic shocks, or any time when the capacitor(s) are charged sufficiently. In any case, an ideal charge time associated with the capacitor(s) is extrapolated from a first measured charge interval associated with charging the capacitor(s) to a first energy level. By extrapolating the first charge time to estimate an ideal charge time associated with charging the one or more capacitors to a second energy level, a fairly accurate estimate of the ideal charge time is obtained. Then, the actual charge time associated with charging the capacitor(s) to a second energy level, e.g., the fully charged state, is also measured. The deformation factor is calculated as a ratio of the actual charge time to the second energy level to the ideal charge time to the second energy level. In some cases, the calculated deformation factor is used to adjust the timing of a future scheduled reformation of the capacitor(s).

Figure 1:
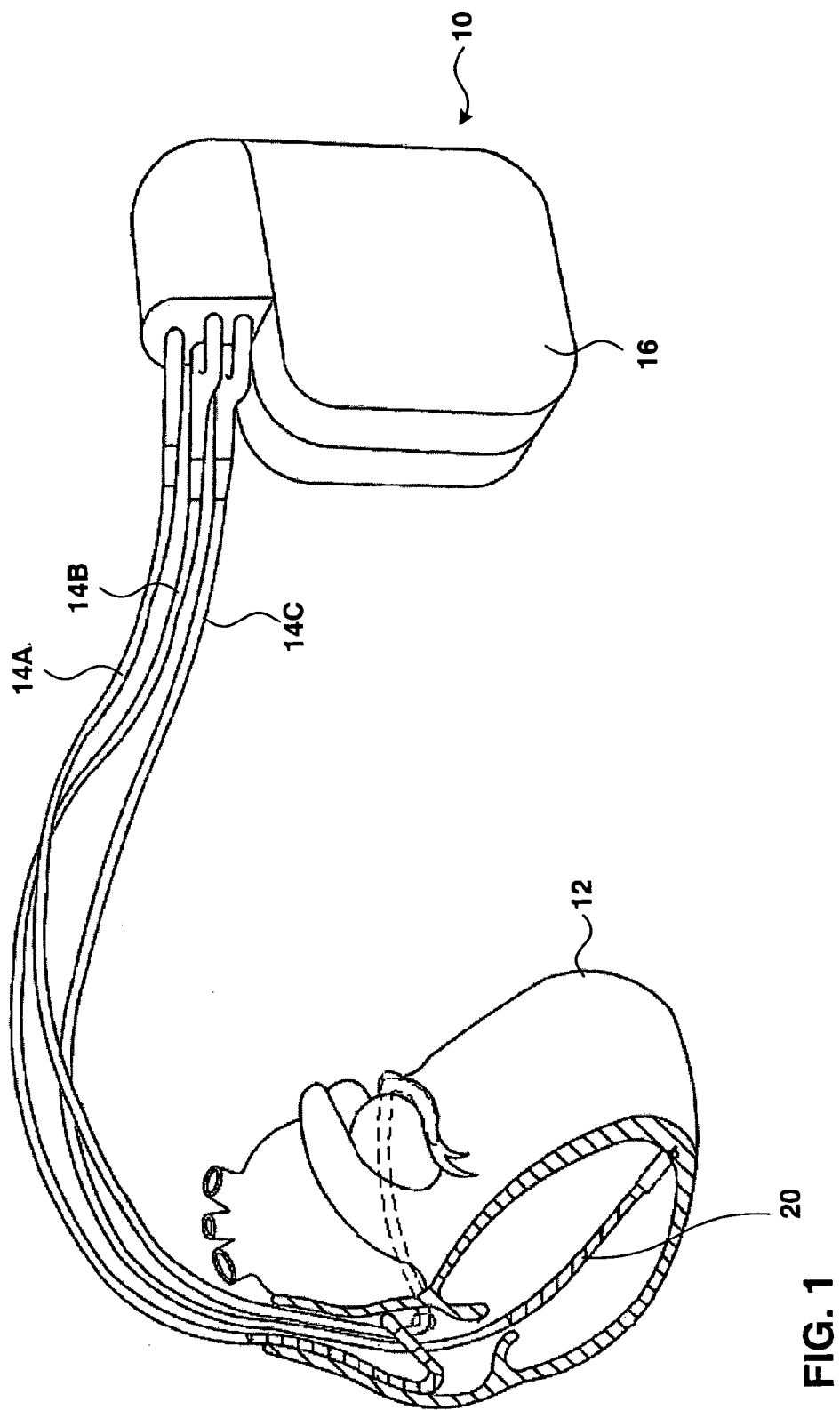
FIG. 1 is a conceptual diagram illustrating an example implantable medical device (IMD) capable of implementing aspects of the invention.

FIG. 1 is a schematic representation of an exemplary IMD 10 capable of implementing one or more aspects of the invention. In this example, IMD 10 is a three channel pacing device shown in conjunction with a human heart 12. IMD 10 also includes cardioversion and defibrillation functionality and may be referred to as a pacemaker-cardioverter-defibrillator (PCD). In accordance with the invention, IMD 10 generally houses one or more high-voltage capacitors that are subject to deformation, and therefore require reformation in order to ensure that the high-voltage capacitors will function properly, when needed.

As shown in FIG. 1, by way of example, IMD 10 includes left ventricular (LV) coronary sinus lead 14A, which is passed through a vein into the right atrium of heart 12, into the coronary sinus and then inferiorly into the great vein and cardiac veins extending from the coronary sinus to deploy the distal ring pace/sense electrodes alongside the LV chamber. The distal end of LV coronary sinus lead 14A positions ring electrodes with respect to the adjacent wall of the left ventricle. Right ventricular (RV) lead 14C is passed through the vein that leads into the right atrium and feeds into the right ventricle where its distal ring and tip pace/sense electrodes are fixed in place in the apex or in the interventricular septum. Right atrium (RA) lead 14B is positioned within the RA chamber, with distal end of RA lead 14B positioning ring electrodes with respect to the adjacent wall of the right atrium or positioned within the atrial appendage. The different leads may include electrodes for pacing and, in accordance with the invention, one or more of leads 14 position high voltage electrodes for delivery of cardioversion or defibrillation shocks using the one or more high-voltage capacitors within IMD 10.

In general, each lead 14 includes electrodes, which IMD 10 uses to sense electrical signals attendant to the depolarization and repolarization of heart 12. In some embodiments, IMD 10 uses these electrodes on leads 14 to provide pacing pulses to heart 12, although the invention is not limited in that respect. For example, electrodes used for sensing and pacing can be unipolar or bipolar, as is well known in the art.

In accordance with the invention, IMD 10 is capable of defibrillation or cardioversion therapy, via electrodes located on leads 14. For example, IMD 10 detects ventricular fibrillation of heart 12, and deliver defibrillation therapy to heart 12 in the form of electrical shocks. In that case, one or more high voltage capacitors within IMD 10 are rapidly charged to a desired energy level, and then discharged to deliver the defibrillation shock to heart 12. By way of example, defibrillation electrode 20 disposed on lead 14C may be used to deliver such shocks. Housing 16 of IMD 10 functions as the ground electrode when shocks are delivered to defibrillation electrode 20.

In order to ensure that the capacitors within IMD 10 can be properly charged for delivery of defibrillation or cardioversion shocks, capacitor reformation processes are performed. Moreover, in accordance with the invention, a deformation factor is calculated during the reformation as described in greater detail below. In some cases, the calculated deformation factor is used to schedule a future reformation process.

Figure 2:
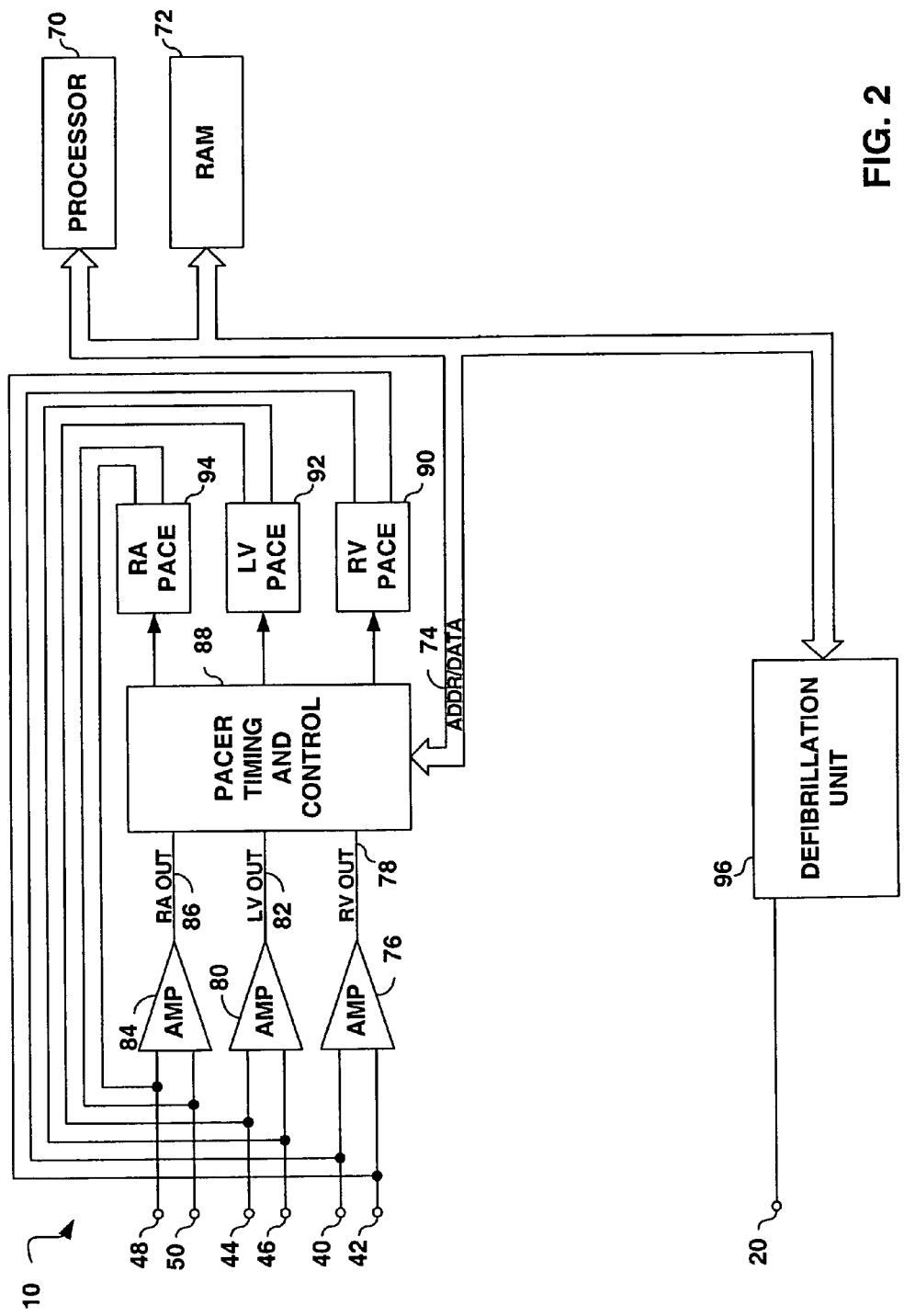
FIG. 2 is a functional block diagram of the IMD illustrated in FIG. 1.

FIG. 2 is a is a functional block diagram of exemplary IMD 10. As shown in FIG. 2, IMD 10 can take the form of a multi-chamber PCD having a microprocessor-based architecture. However, this diagram should be taken as exemplary of one specific device in which various embodiments of the invention may be embodied, and not as limiting. In other words, the techniques described herein may also be executed in other types of IMDs.

In the example of FIG. 2, IMD 10 includes a processor 70, e.g., a microprocessor. Processor 70 executes program instructions stored in memory, such as a ROM (not shown), EEPROM (not shown), and/or RAM 72, which control processor 70 to perform the functions ascribed to processor 70. Processor 70 is coupled to various other components of IMD 10 via an address/data bus 74, e.g., to communicate with and/or control the other components. Various other components may also be included in IMD 10, if desired.

In general, IMD 10 senses electrical activity within heart 12. Electrodes 40 and 42 are coupled to amplifier 76, which comprises an automatic gain controlled amplifier providing an adjustable sensing threshold as a function of the measured R-wave amplitude. For example, electrodes 40, 42 are disposed on lead 14C (FIG. 1). A signal is generated on RV out line 78 whenever the signal sensed between electrodes 40 and 42 exceeds a sensing threshold. Thus, electrodes 40 and 42 and amplifier 76 are used to detect intrinsic right ventricular depolarizations.

Electrodes 44 and 46 are coupled to amplifier 80, which also comprises an automatic gain controlled amplifier providing an adjustable sensing threshold as a function of measured R-wave amplitude. For example, electrodes 44, 46 are disposed on lead 14A (FIG. 1). A signal is generated on LV out line 82 whenever the signal sensed between electrodes 44 and 46 exceeds a sensing threshold. Thus, electrodes 44 and 46 and amplifier 80 are used to detect intrinsic left ventricular depolarizations.

Electrodes 48 and 50 are coupled to amplifier 84, which comprises an automatic gain controlled amplifier providing an adjustable sensing threshold as a function of the measured P-wave amplitude. For example, electrodes 40, 42 are disposed on lead 14B (FIG. 1). A signal is generated on RA out line 86 whenever the signal between electrodes 48 and 50 exceeds a sensing threshold. Thus, electrodes 48 and 50 and amplifier 84 are used to detect intrinsic atrial depolarizations.

In some embodiments, IMD 10 paces heart 12. In such embodiments, output circuits 90, 92, 94 deliver pacing pulses to heart 12 via electrodes 40–50 under the control of pacer timing/control circuitry 88. Specifically, output circuit 90 is coupled to electrodes 40 and 42 to deliver pacing pulses to the right ventricle, output circuit 92 is coupled to electrodes 44 and 46 to deliver pacing pulses to the left ventricle, and output circuit 94 is coupled to electrodes 48 and 50 to deliver pacing pulses to the right atrium. Output circuits 90–94, for example, include capacitors and switches for the storage and delivery of energy as a pacing pulse.

Pacer timing/control circuitry 88 includes programmable digital counters, which control the basic time intervals associated with modes of pacing. Circuitry 88 also controls escape intervals associated with pacing. Circuitry 88 resets interval counters upon detection of R-waves or P-waves, or generation of pacing pulses, and thereby controls the basic timing of cardiac pacing functions.

Intervals defined by pacing circuitry 88 include refractory periods during which sensed R-waves and P-waves are ineffective to restart timing of escape intervals, and the pulse widths of the pacing pulses. The durations of these intervals are determined by processor 70 in response to data stored in RAM 72, and are communicated to circuitry 88 via address/data bus 74. The amplitude of the cardiac pacing pulses is also determined by circuitry 88 under control of processor 70.

Processor 70 operates as an interrupt driven device, and is responsive to interrupts from pacer timing/control circuitry 88 corresponding to the occurrence of sensed P-waves and R-waves and corresponding to the generation of cardiac pacing pulses. Those interrupts are provided via data/address bus 76. Any necessary mathematical calculations to be performed by processor 70 and any updating of the values or intervals controlled by pacer timing/control circuitry 88 take place following such interrupts.

IMD 10 also detects ventricular and/or atrial fibrillations of heart 12 using fibrillation detection algorithms known in the art. For example, processor 70 detects ventricular fibrillation based on R-wave indications received from circuitry 88 by detecting a sustained series of short R-R intervals of an average rate indicative of fibrillation, or an unbroken series of short R—R intervals. Processor 70 can employ single or multiple zone detection techniques.

IMD 10 delivers defibrillation shocks to heart 12 via one or more of defibrillation electrodes 20 in response to detected fibrillation. For example, electrode 20 is coupled to a defibrillation unit 96, which delivers defibrillation shocks under the control of processor 70. Defibrillation unit 96 includes one or more high-voltage capacitors, one or more switches for coupling the capacitors to electrode 20 and possibly other defibrillation electrodes. Processor 70 employs an escape interval counter to control timing of defibrillation shocks, as well as associated refractory periods. In some embodiments, processor 70 also controls the delivery of cardioversion shocks by defibrillation unit 96.

In order to ensure that the high-voltage capacitors within defibrillation unit 96 can be properly charged for delivery of defibrillation or cardioversion shocks, capacitor reformation processes are performed in IMD 10. In particular, processor 70 directs the reformation process at specific scheduled times, e.g., every three months or so. During reformation, in accordance with the invention, a deformation factor is calculated by processor 70 as described in greater detail below. Alternatively, the deformation factor can be calculated at other times, e.g., during a process of charging the capacitors to deliver therapeutic shocks. In some cases, the calculated deformation factor is used to adjust the scheduling of a future reformation process in order to balance a desire to reform the capacitors to ensure adequate charging can be achieved, with a desire to avoid reformation and thereby extend the useful life of the capacitors.

Figure 3:
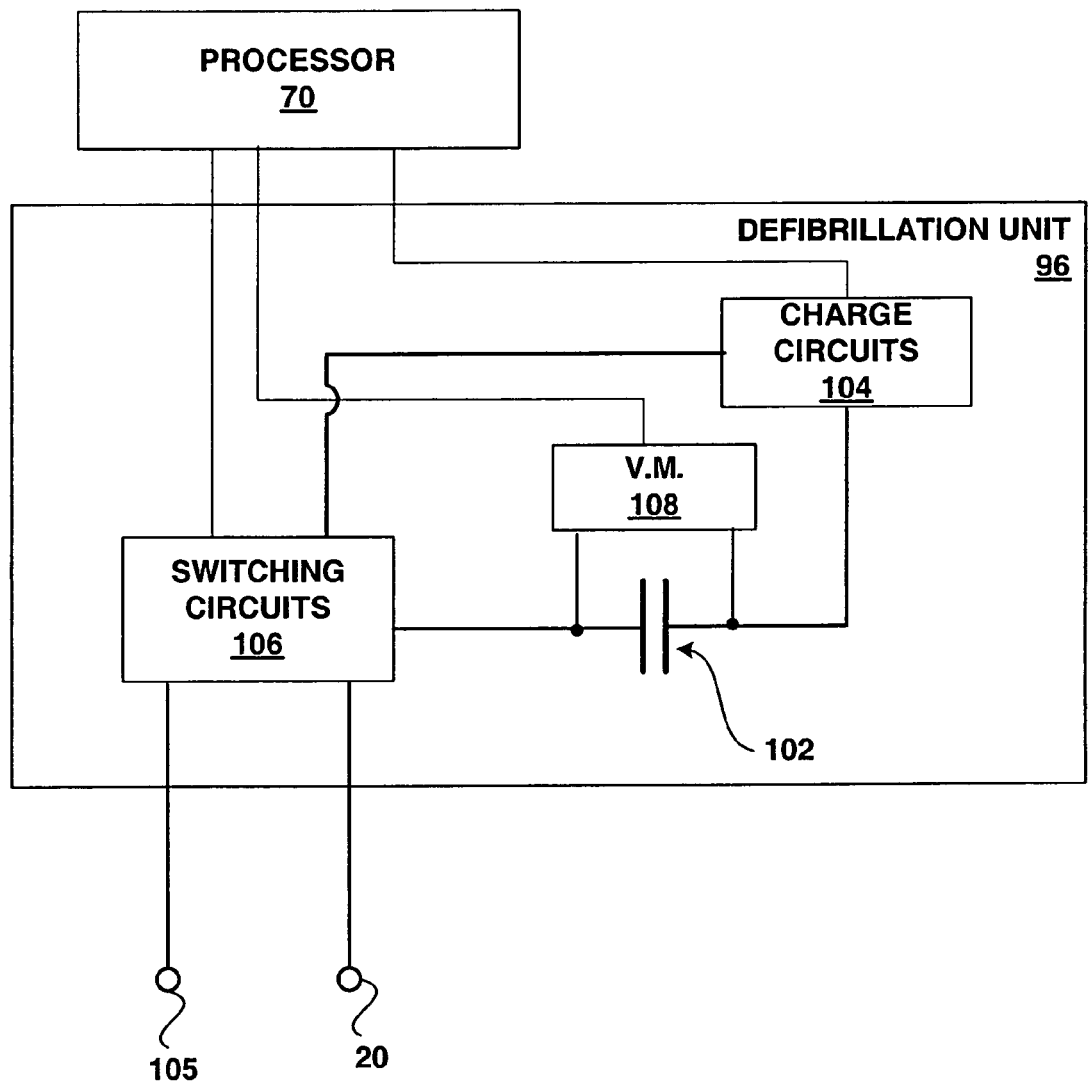
FIG. 3 is another functional block diagram illustrating a defibrillation unit coupled to a processor according to an embodiment of the invention.

FIG. 3 is another functional block diagram illustrating a defibrillation unit 96 coupled to a processor 70 according to an embodiment of the invention. Defibrillation unit 96 includes one or more capacitors 102 (hereafter capacitors 102) capable of storing charge sufficient to deliver defibrillation shocks. At the direction of processor 70, charge circuits 104 charge capacitors 102 to desired energy levels. Processor 70 controls switching circuits 106 in order to discharge capacitors 102 to deliver defibrillation shocks to one or more defibrillation electrodes 20 (FIG. 2).

In accordance with the invention, processor 70 directs a reformation process in order to reform capacitors 102, e.g., following extended periods of inactivity. In that case, processor directs charge circuits 104 to charge capacitors 102 to a fully charged state, which repairs capacitors 102 by rebuilding oxide layers, or the like. Following reformation, processor 70 invokes switching circuits 106 to drain the energy from capacitors 102 without delivering defibrillation shocks. For example, switching circuits 106 may include resistors to drain the energy from capacitors 102 without delivering defibrillation shocks following reformation. Alternatively, residual charge from the reformation may remain on capacitors 102 for an extended period.

A charge measurement device such as volt meter 108, or the like, is used to measure charge across capacitors 102. During reformation, processor 70 tracks the time it takes capacitors 102 to charge to a desired level. In particular, processor 70 measures the amount of time it takes to charge capacitors 102 to a first energy level, e.g., approximately eight joules. Processor 70 implements a timer that is invoked when charge circuits 104 begin charging capacitors 102. Once volt meter 108 determines that capacitors 102 have been charged to the first energy level, processor 70 records a time interval associated with charging capacitors 102 to the first energy level.

The phenomenon of capacitor deformation typically manifests at higher energy levels, e.g., greater than eight joules. Therefore, in order to estimate an ideal charge time associated with charging capacitors 102 to a second energy level, e.g., approximately thirty-two joules, processor 70 extrapolates the measured charge interval through eight joules to the second energy level.

Processor 70 also measures the actual charge interval that it takes to charge capacitors 102 to the second energy level. Processor 70 uses these measurements to calculate a deformation factor associated with capacitors 102. In particular, processor 70 calculates the deformation factor as a ratio of the measured time interval that it takes to charge capacitors 102 to the second energy level to the extrapolated ideal charge time.

Calculating the deformation factor in this manner can achieve several advantages. For example, the deformation factor is calculated without knowledge of the actual ideal charge time. Also, the deformation factor is calculated internal to IMD 10, which is useful because IMD 10 is implanted. Moreover, in accordance with the invention, the calculated deformation factor accounts for battery or power depletion within charge circuits 104. Accordingly, the calculated deformation factor should be an accurate representation of changes in the charge time associated with capacitors 102.

Once processor 70 has calculated the deformation factor associated with capacitors 102, processor 70 uses the calculated deformation factor in order to improve subsequent reformations. In particular, processor 70 adjusts a scheduled time associated with a next reformation process based on the deformation factor. For example, processor 70 may determine whether the deformation factor is greater than a threshold and reduce the scheduled time associated with the next reformation process if the deformation factor is greater than the threshold. In addition, processor 70 may determine whether the deformation factor is less than a threshold and increases the scheduled time associated with the next reformation process if the deformation factor is less than the threshold. Alternatively, processor 70 may adjust the scheduled time associated with a next reformation process in a manner substantially proportionate to the deformation factor.

The process of calculating the deformation factor can also be performed when capacitors 102 are charged to deliver therapeutic shocks, particularly if the charging of capacitors 102 is sufficient to achieve the second energy level. In that case, following the charging of capacitors 102 and calculation of the deformation factor, a therapeutic shock is delivered. In order to deliver a therapeutic shock, processor 70 causes switching circuits to discharge capacitors 102, causing a shock to be delivered across electrodes 20 and 105. For example, electrode 105 may correspond to housing 16 of IMD 10 (FIG. 1). As yet another variation, processor 70 could be programmed or configured to adjust a scheduled reformation following the process of charging capacitors 102 and delivery of a therapeutic shock. In particular, the adjustments to reformation scheduling can be based on a calculated deformation factor calculated during the shock delivery process. In other words, future reformations could be avoided or rescheduled following the charging of capacitors 102, calculation of the deformation factor and delivery of a therapeutic shock.

Figure 4:
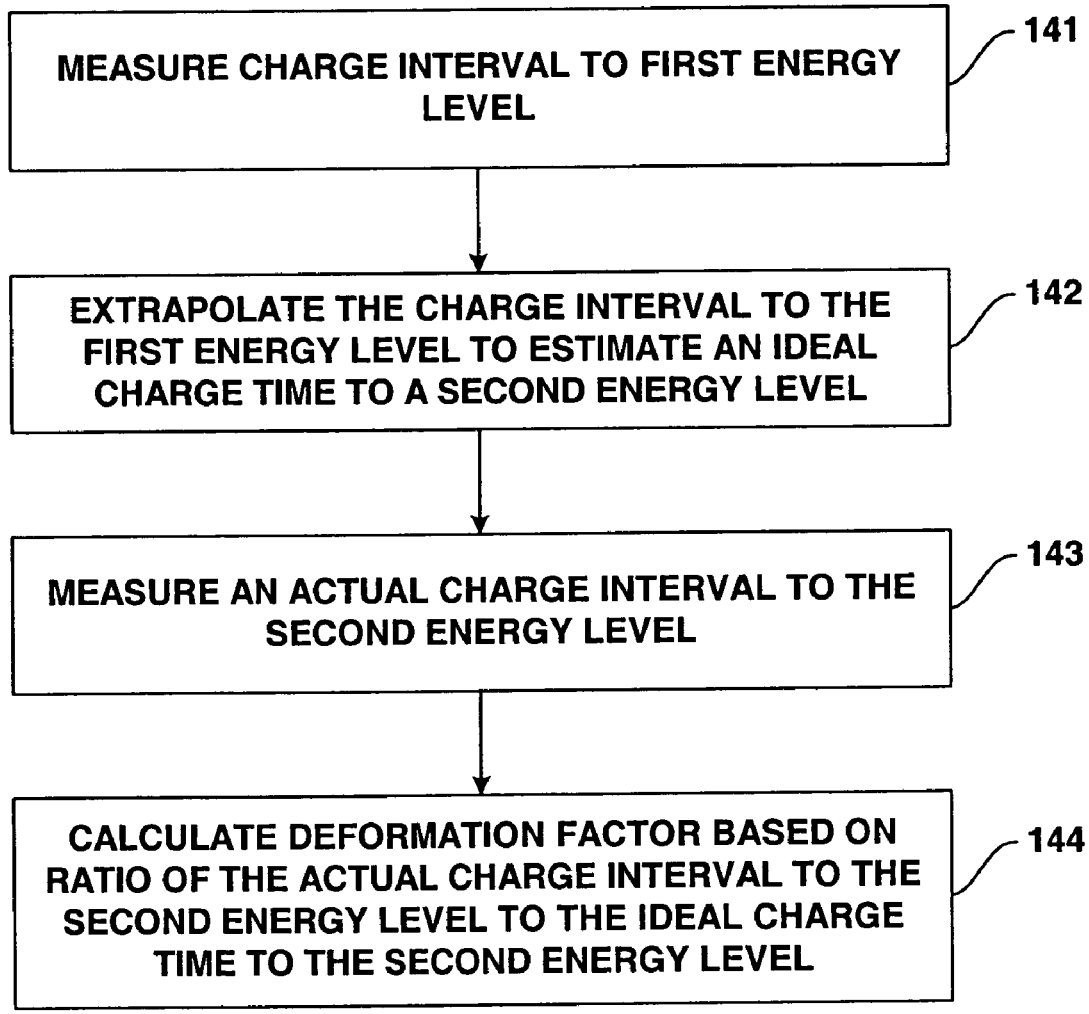
FIG. 4 is a flow diagram illustrating a process according to an embodiment of the invention.

FIG. 4 is a flow diagram illustrating a process according to an embodiment of the invention. As shown in FIG. 4, processor 70 measures a charge interval associated with charging capacitors 102 to a first energy level (141). For example, processor 70 invokes and monitors volt meter 108 in order to determine when capacitors 102 are charged to the first energy level, and records time associated with the charge interval to the first energy level. Processor 70 then extrapolates the charge interval to the first energy level to estimate an ideal charge time to a second energy level (142).

Processor 70 also measures an actual charge interval associated with charging capacitors 102 to the second energy level (143). Processor 70 invokes and monitors volt meter 108 in order to determine when capacitors 102 are charged to the second energy level, and records time associated with the charge interval to the second energy level. Processor 70 then calculates a deformation factor as a ratio of the actual measured charge interval to the second energy level to the ideal charge time (144). In this manner, the deformation factor is calculated internal to IMD 10, without knowledge of the actual ideal charge time. Moreover, the technique automatically accounts for depletion effects associated with batteries or other power sources of charge circuits 104.

Figure 5:
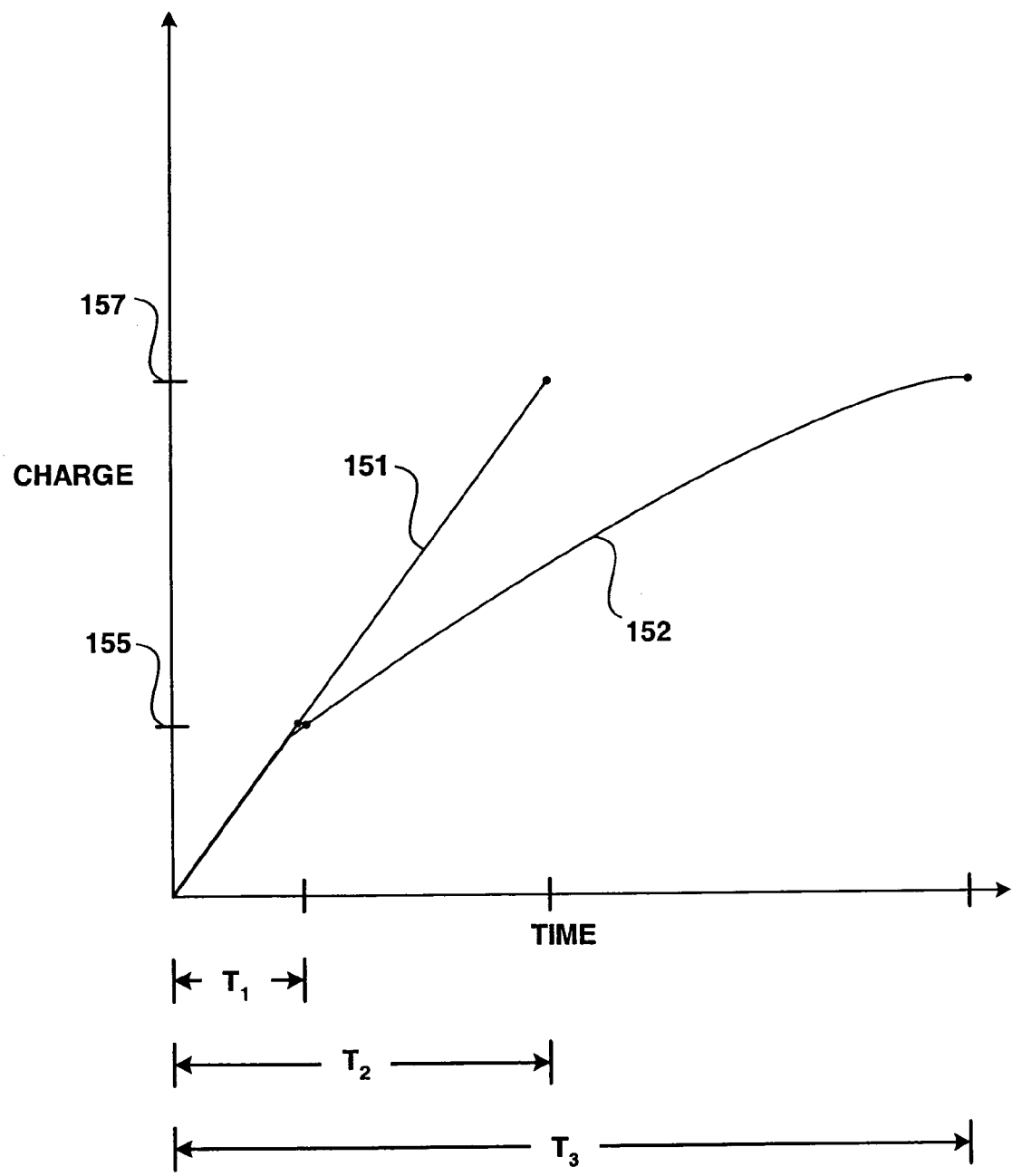
FIG. 5 is a graph conceptually illustrating an extrapolation technique that can be used in calculating a deformation factor in accordance with an embodiment of the invention.

FIG. 5 is graph conceptually illustrating an extrapolation technique used in calculating a deformation factor in accordance with an embodiment of the invention. In particular, line 151 can be viewed as a theoretical charge function indicative of the theoretical time it takes to charge one or more capacitors to various levels of charge. Line 152 can be viewed as an actual charge function indicative of the actual time it takes to charge on or more capacitors to various levels of charge. As can be appreciated from lines 151 and 152, deformation effects typically do not manifest at lower energies of charge. Accordingly, lines 151 and 152 are substantially similar at low levels of charge, but significantly differ at higher levels of charge.

In accordance with the invention, time ($T_1$) represents a measured time associated with charging capacitors 102 to a first level of charge 155. The first level of charge 155, for example, may be approximately eight joules. Lines 151 and 152 are substantially similar at these low levels of charge. Accordingly, below the first level of charge 155, line 152 is a relatively accurate representation of ideal charge transfer. Accordingly, the remaining portion of line 151 is extrapolated based on the measured time associated with charging capacitors 102 to a first level of charge 155. In other words, the general nature and slope of line 152 below the first level of charge 155 is extended to create ideal charge line 151 that extends to a second level of charge 157. An ideal charge time ($T_2$) to the second level of charge 157 is obtained from the extrapolation. Line 151 may be a straight line, but the invention is not necessarily limited in that respect. By way of example, the second level of charge 157 may be approximately thirty-two joules.

Again, deformation effects manifest at higher energies of charge. Accordingly, the slope of line 152 generally decreases as energy levels exceed the first level of charge 155. Time ($T_3$) represents an actual or measured time associated with charging capacitors 102 to the second level of charge 157. In accordance with the invention, processor 70 calculates a deformation factor as the ratio ($T_3$)/($T_1$). In this manner, the deformation factor is calculated internal to IMD 10, without knowledge of the actual ideal charge time. Moreover, the calculated deformation factor automatically accounts for depletion effects associated with batteries or other power sources of charge circuits 104.

Figure 6:
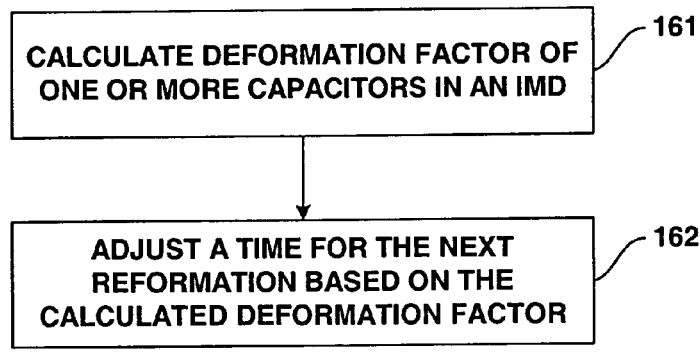
FIGS. 6–8 are additional flow diagrams illustrating processes according to embodiments of the invention.

FIG. 6 is a flow diagram illustrating a process according to an embodiment of the invention. As shown in FIG. 6, processor 70 calculates a deformation factor of one or more capacitors 102 in IMD 10 (161). Processor 70 then adjusts a time for the next reformation based on the calculated deformation factor (162). For example, processor 70 may determine whether the deformation factor is greater than a threshold and reduce the scheduled time associated with the next reformation process if the deformation factor is greater than the threshold. In addition, processor 70 may determine whether the deformation factor is less than a threshold and increase the scheduled time associated with the next reformation process if the deformation factor is less than the threshold.

Alternatively, processor 70 may adjust the scheduled time associated with a next reformation process in a manner substantially proportionate to the deformation factor. In any case, by adjusting the time for the next reformation based on the calculated deformation factor, processor 70 balances the desire to reform capacitors 102 in order to ensure that capacitors 102 are always able to charge quickly enough for effective delivery of defibrillation, with the desire to avoid excessive reformations which reduce the effective life of capacitors 102.

Figure 7:
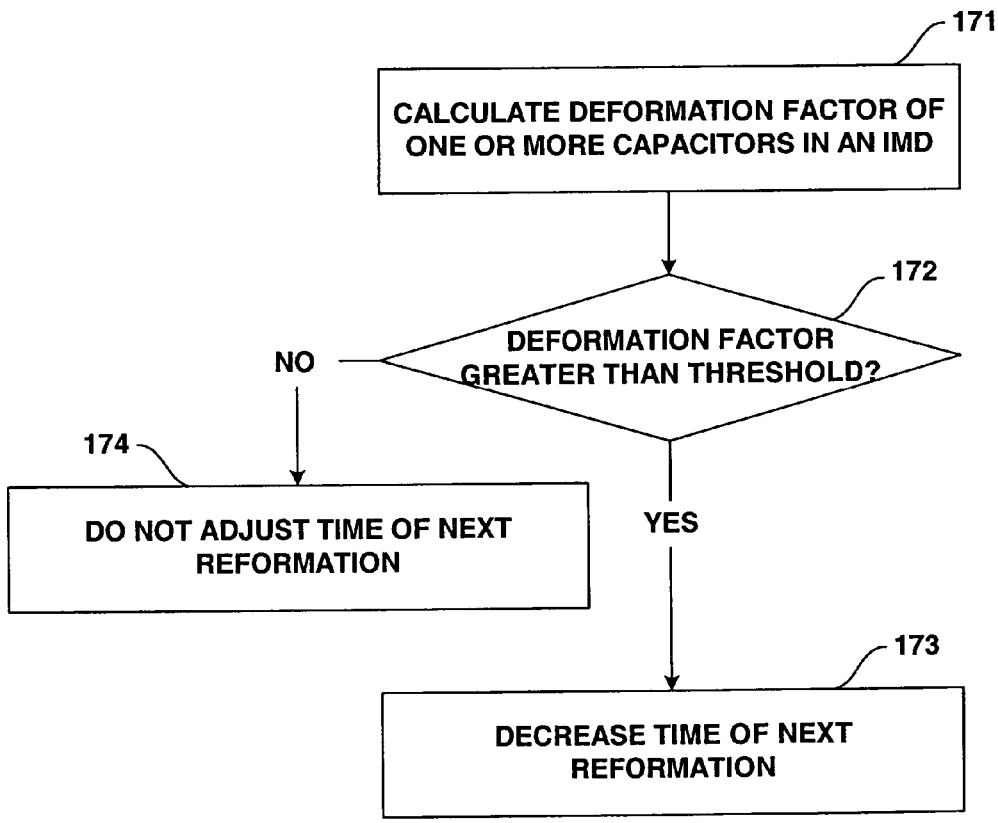

FIG. 7 is a flow diagram illustrating a process according to an embodiment of the invention. As shown in FIG. 7, processor 70 calculates a deformation factor of one or more capacitors 102 in IMD 10 (171). Processor 70 then determines whether the calculated deformation factor is greater than a threshold (172). For example, the threshold may be approximately 1.5, although the invention is not limited in that respect. If the deformation factor is greater than the threshold (yes branch of 172), processor 70 decreases a time for the next reformation (173). The time reduction for the next reformation may be fixed or variably proportionate to the calculated deformation factor. In the embodiment of FIG. 7, if the deformation factor is not greater than the threshold (no branch of 172), processor 70 does not decrease the time for the next reformation.

Figure 8:
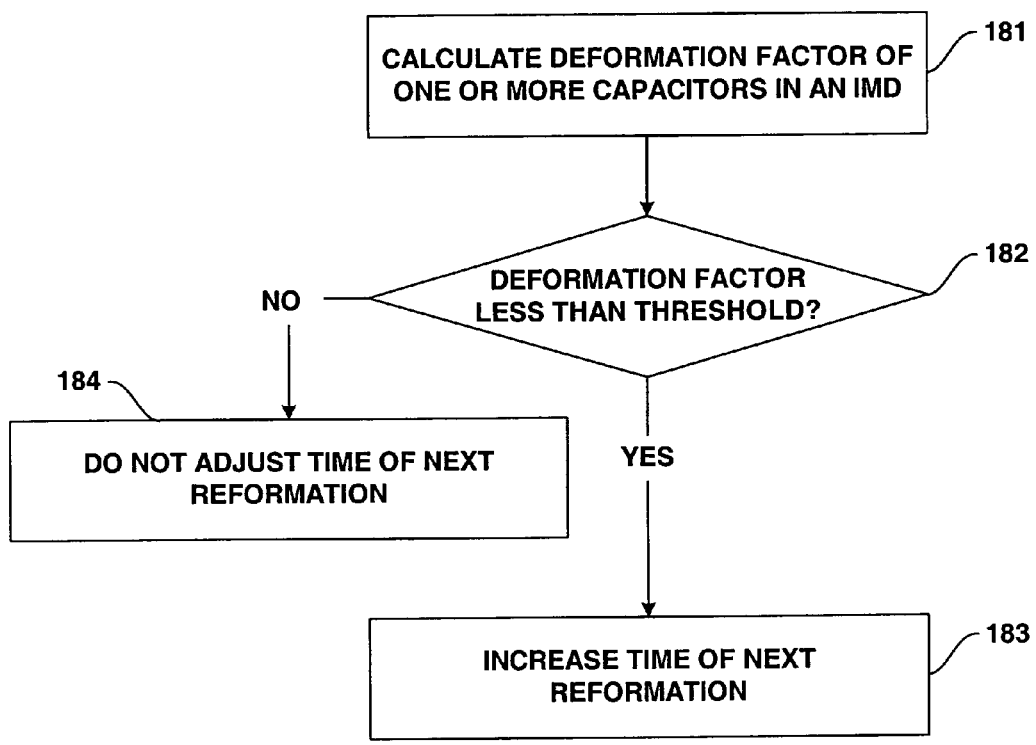

FIG. 8 is another flow diagram illustrating a process according to an embodiment of the invention. As shown in FIG. 8, processor 70 calculates a deformation factor of one or more capacitors 102 in IMD 10 (181). Processor 70 then determines whether the calculated deformation factor is less than a threshold (182). For example, the threshold may be approximately 1.5, although the invention is not limited in that respect. Alternatively, different thresholds can be established for the processes of FIGS. 7 and 8.

If the deformation factor is less than the threshold (yes branch of 182), processor 70 increases a time for the next reformation (183). The time increase for the next reformation may be fixed or variably proportionate to the calculated deformation factor. In the embodiment of FIG. 8, if the deformation factor is not greater than the threshold (no branch of 182), processor 70 does not increase the time for the next reformation. Combinations of the techniques of FIGS. 7 and 8 may also be used, e.g., increasing a time for the next reformation if the deformation factor is less than a first threshold and decreasing a time for the next reformation if the deformation factor is greater than a second threshold.

Various embodiments of the invention have been described. For example, techniques for estimating deformation factors of capacitors in IMDs have been described, and various techniques for using the calculated deformation factors in IMDs have also been described. Although aspects of the invention have been described in the context of defibrillation capacitors, the same concepts can be applied to any capacitors of an IMD that are subject to deformation. Moreover, although many techniques of calculating the deformation factor have been described in the context of a reformation process, the same techniques may be applied at other times, such as during a process of charging the capacitors in order to deliver a therapeutic shock. As yet another variation, the IMD could be programmed or configured to adjust a scheduled reformation following the process of charging the capacitors in order to deliver a therapeutic shock, e.g., based on a calculated deformation factor calculated during the process.

The techniques described herein may be implemented in an IMD in hardware, software, firmware, or the like. Example hardware implementations include implementations by a digital signal processor (DSP), an application specific integrated circuit (ASIC), a field programmable gate array (FPGA), a programmable logic device, specifically designed hardware components, or any combination thereof. In addition, one or more of the techniques described herein may be partially or wholly executed in software. In that case, a computer-readable medium stores or otherwise comprises computer-readable instructions, i.e., program code, that are executed by a processor or DSP of an IMD to carry out one of more of the techniques described above.

For example, the computer-readable medium may comprise random access memory (RAM), read-only memory (ROM), non-volatile random access memory (NVRAM), electrically erasable programmable read-only memory (EEPROM), flash memory, or the like. In that case, the computer-readable medium is coupled to processor 70 of IMD 10 via bus 74. RAM 72 is one example of such a computer-readable medium. These and other embodiments are within the scope of the following claims.

The invention claimed is:

1. A method for estimating a deformation factor in an IMD comprising:
   measuring a first charge interval associated with charging one or more capacitors of an implantable medical device to a first energy level;
   extrapolating the first charge interval to estimate an ideal charge time associated with charging the one or more capacitors to a second energy level;
   measuring a second charge interval associated with charging the one or more capacitors to the second energy level; and
   generating a deformation factor as a ratio of the second charge interval to the ideal charge time.

2. The method of claim 1, wherein the method is performed during a reformation process applied to the one or more capacitors.

3. The method of claim 1, wherein the method is performed during a therapeutic process of charging the one or more capacitors in order to deliver a therapeutic shock.

4. The method of claim 1, further comprising adjusting a scheduled time associated with a next reformation process based on the deformation factor.

5. The method of claim of claim 4, further comprising determining whether the deformation factor is greater than a threshold and reducing the scheduled time associated with the next reformation process if the deformation factor is greater than the threshold.

6. The method of claim 4, further comprising adjusting the scheduled time associated with a next reformation process in a manner substantially proportionate to the deformation factor.

7. The method of claim of claim 4, further comprising determining whether the deformation factor is less than a threshold and increasing the scheduled time associated with the next reformation process if the deformation factor is less than the threshold.

8. A method for estimating a deformation factor in am IMD comprising:
   calculating a deformation factor associated with one or more capacitors in an implantable medical device; and
   adjusting a scheduled time associated with a next reformation process on the one or more capacitors based on the deformation factor.

9. The method of claim of claim 8, further comprising determining whether the deformation factor is greater than a threshold and reducing the scheduled time associated with the next reformation process if the deformation factor is greater than the threshold.

10. The method of claim 8, further comprising adjusting the scheduled time associated with a next reformation process in a manner substantially proportionate to the deformation factor.

11. The method of claim of claim 8, further comprising determining whether the deformation factor is less than a threshold and increasing the scheduled time associated with the next reformation process if the deformation factor is less than the threshold.

12. The method of claim 1, wherein calculating the deformation factor includes:
   measuring a first charge interval associated with charging the one or more capacitors to a first energy level;
   extrapolating the first charge interval to estimate an ideal charge time associated with charging the one or more capacitors to a second energy level;
   measuring a second charge interval associated with charging the one or more capacitors to the second energy level; and
   generating a deformation factor as a ratio of the second charge interval to the ideal charge time.

13. An implantable medical device comprising:
   one or more capacitors;
   a charge circuit to charge the one or more capacitors;
   a charge measurement device to measure charge across the one or more capacitors; and
   a processor to measure a first charge interval associated with charging the one or more capacitors a first energy level, extrapolate the first charge interval to estimate an ideal charge time associated with charging the one or more capacitors to a second energy level, measure a second charge interval associated with charging the one or more capacitors to the second energy level, and generate a deformation factor as a ratio of the second charge interval to the ideal charge time.

14. The implantable medical device of claim 13, wherein the one or more capacitors are defibrillation capacitors, the device further comprising one or more defibrillation electrodes electrically coupled to the one or more capacitors.

15. The implantable medical device of claim 13, wherein the processor adjusts a scheduled time associated with a next reformation process on the one or more capacitors based on the deformation factor.

16. An implantable medical device comprising:
   one or more capacitors;
   a charge circuit to charge the one or more capacitors;
   a charge measurement device to measure charge across the one or more capacitors; and
   a processor to calculate a deformation factor of the one or more capacitors, and adjust a scheduled time associated with a next reformation process on the one or more capacitors based on the deformation factor.

17. The implantable medical device of claim 16, wherein the processor determines whether the deformation factor is greater than a threshold and reduces the scheduled time associated with the next reformation process if the deformation factor is greater than the threshold.

18. The implantable medical device of claim 16, wherein the processor adjusts the scheduled time associated with a next reformation process in a manner substantially proportionate to the deformation factor.

19. The implantable medical device of claim 16, wherein the processor determines whether the deformation factor is less than a threshold and increasing the scheduled time associated with the next reformation process if the deformation factor is less than the threshold.

20. A computer-readable medium comprising executable instructions that when executed in an implantable medical device cause the device to:
   measure a first charge interval associated with charging one or more capacitors of the implantable medical device to a first energy level;
   extrapolate the first charge interval to estimate an ideal charge time associated with charging the one or more capacitors to a second energy level;
   measure a second charge interval associated with charging the one or more capacitors to the second energy level; and
   generate a deformation factor as a ratio of the second charge interval to the ideal charge time.

21. The computer-readable medium of claim 20, further comprising instructions that when executed cause the device to adjust a scheduled time associated with a next reformation process based on the deformation factor.

22. A computer-readable medium comprising executable instructions that when executed in an implantable medical device cause the device to:
calculate a deformation factor associated with one or more capacitors in the implantable medical device; and
adjust a scheduled time associated with a next reformation process on the one or more capacitors based on the deformation factor.

23. The computer-readable medium of claim 22, further comprising instructions that when executed cause the device to determine whether the deformation factor is greater than a threshold and reduce the scheduled time associated with the next reformation process if the deformation factor is greater than the threshold.

24. The computer-readable medium of claim 22, further comprising instructions that when executed cause the device to adjust the scheduled time associated with a next reformation process in a manner substantially proportionate to the deformation factor.

25. The computer-readable medium of claim 22, further comprising instructions that when executed cause the device to determine whether the deformation factor is less than a threshold and increase the scheduled time associated with the next reformation process if the deformation factor is less than the threshold.

26. An implantable medical device comprising:
one or more capacitors;
means for charging the one or more capacitors;
means for measuring charge across the one or more capacitors;
means for measuring a first charge interval associated with charging the one or more capacitors a first energy level;
means for extrapolating the first charge interval to estimate an ideal charge time associated with charging the one or more capacitors to a second energy level;
means for measuring a second charge interval associated with charging the one or more capacitors to the second energy level; and
means for generating a deformation factor as a ratio of the second charge interval to the ideal charge time.

27. The implantable medical device of claim 26, further comprising means for adjusting a scheduled time associated with a next reformation process on the one or more capacitors based on the deformation factor.

28. An implantable medical device comprising:
one or more capacitors;
means for charging the one or more capacitors;
means for measuring charge across the one or more capacitors;
means for calculating a deformation factor of the one or more capacitors; and
means for adjusting a scheduled time associated with a next reformation process on the one or more capacitors based on the deformation factor.

29. The implantable medical device of claim 28, further comprising:
means for determining whether the deformation factor is greater than a threshold; and
means for reducing the scheduled time associated with the next reformation process if the deformation factor is greater than the threshold.

30. The implantable medical device of claim 28, further comprising means for adjusting the scheduled time associated with a next reformation process in a manner substantially proportionate to the deformation factor.

31. The implantable medical device of claim 28, further comprising:
means for determining whether the deformation factor is less than a threshold; and
means for increasing the scheduled time associated with the next reformation process if the deformation factor is less than the threshold.

* * * * *